United States Patent
Beak et al.

(10) Patent No.: US 11,640,662 B2
(45) Date of Patent: May 2, 2023

(54) SOMATIC MUTATION DETECTION APPARATUS AND METHOD WITH REDUCED SEQUENCING PLATFORM-SPECIFIC ERROR

(71) Applicant: SEOUL NATIONAL UNIVERSITY R&DB FOUNDATION, Seoul (KR)

(72) Inventors: Dae Hyun Beak, Seoul (KR); Jun Hak Ahn, Seoul (KR); Hyeon Seong Jeon, Seoul (KR); Do Yeon Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 303 days.

(21) Appl. No.: 17/261,164

(22) PCT Filed: Oct. 25, 2019

(86) PCT No.: PCT/KR2019/014109
§ 371 (c)(1),
(2) Date: Jan. 18, 2021

(87) PCT Pub. No.: WO2021/080043
PCT Pub. Date: Apr. 29, 2021

(65) Prior Publication Data
US 2022/0108438 A1   Apr. 7, 2022

(51) Int. Cl.
*G06T 7/00* (2017.01)
*G16B 20/20* (2019.01)
(Continued)

(52) U.S. Cl.
CPC ............. *G06T 7/0012* (2013.01); *G06N 3/08* (2013.01); *G06V 10/40* (2022.01); *G16B 20/20* (2019.02);
(Continued)

(58) Field of Classification Search
CPC ......... G06T 7/0012; G06T 2207/20081; G06T 2207/20084; G06T 2207/30072;
(Continued)

(56) References Cited

U.S. PATENT DOCUMENTS 6,260,034 B1 * 7/2001 Bjorkesten ........... G06V 30/194
706/45
10,354,747 B1 * 7/2019 DePristo ................ G16B 40/20
(Continued)

FOREIGN PATENT DOCUMENTS

| KR | 10-2012-0056312 A | 6/2012 |
| KR | 10-1889724 B1 | 8/2018 |
| WO | 98/54669 A1 | 12/1998 |

OTHER PUBLICATIONS

International Search Report for PCT/KR2019/014109 dated Jul. 24, 2020 from Korean Intellectual Property Office.
(Continued)

*Primary Examiner* — Van D Huynh
(74) *Attorney, Agent, or Firm* — Revolution IP, PLLC (57) ABSTRACT

A mutation detection apparatus includes a memory configured to store software for implementing a neural network and a processor configured to detect a mutation by executing the software, wherein the processor is configured to generate first genome data extracted from a target tissue and second genome data extracted from a normal tissue, extract image data by preprocessing the first genome data and the second genome data, and detect a mutation of the target tissue on the basis of the image data through the neural network trained to correct a sequencing platform-specific false positive.

14 Claims, 6 Drawing Sheets

(51) Int. Cl.
*G16B 40/20* (2019.01)
*G06V 10/40* (2022.01)
*G06N 3/08* (2023.01)

(52) U.S. Cl.
CPC .... *G16B 40/20* (2019.02); *G06T 2207/20081* (2013.01); *G06T 2207/20084* (2013.01); *G06T 2207/30072* (2013.01); *G06V 2201/04* (2022.01)

(58) Field of Classification Search
CPC .......... G06T 2207/20076; G06T 2207/30024; G06N 3/08; G06N 3/045; G06N 20/00; G06V 10/40; G06V 2201/04; G06V 10/774; G06V 10/82; G16B 20/20; G16B 40/20; G16B 20/30; G16B 35/10; G16B 35/20
USPC ....................................................... 382/129
See application file for complete search history.

(56) References Cited

U.S. PATENT DOCUMENTS

| | | | |
|---|---|---|---|
| 2019/0261854 A1* | 8/2019 | Gelbman | G06V 10/82 |
| 2020/0185055 A1* | 6/2020 | Dubourg-Felonneau | G16B 30/10 |
| 2020/0227137 A1* | 7/2020 | Sanborn | G16B 20/10 |
| 2020/0286587 A1* | 9/2020 | Israeli | G16B 40/30 |
| 2021/0002728 A1* | 1/2021 | Landau | G16B 30/00 |
| 2021/0062265 A1* | 3/2021 | Lodato | C12N 15/1065 |
| 2021/0398605 A1* | 12/2021 | Gao | G06N 3/045 |

OTHER PUBLICATIONS

Sahraeian, S. M. E. et al., "Deep convolutional neural networks for accurate somatic mutation detection", Nature Communications vol. 10, Article No. 1041 (2019), pp. 1-10.

Anzar, I. et al., "NeoMutate: an ensemble machine learning framework for the prediction of somatic mutations in cancer", BMC Medical Genomics, vol. 12, Article No. 63 (2019), pp. 1-14.

* cited by examiner

SOMATIC MUTATION DETECTION APPARATUS AND METHOD WITH REDUCED SEQUENCING PLATFORM-SPECIFIC ERROR

TECHNICAL FIELD

The present disclosure relates to a method and apparatus for detecting a mutation, and more particularly, to a method and apparatus for detecting a mutation using a neural network trained to decrease a sequencing platform-specific error.

BACKGROUND ART

Next-generation sequencing (NGS) may refer to a method of decomposing deoxyribonucleic acid into a plurality of fragments and performing sequencing in parallel. Unlike conventional Sanger sequencing, NGS can analyze multiple DNA fragments at the same time, and thus can be advantageous in terms of analysis time, analysis cost, and analysis accuracy.

Figure 1:
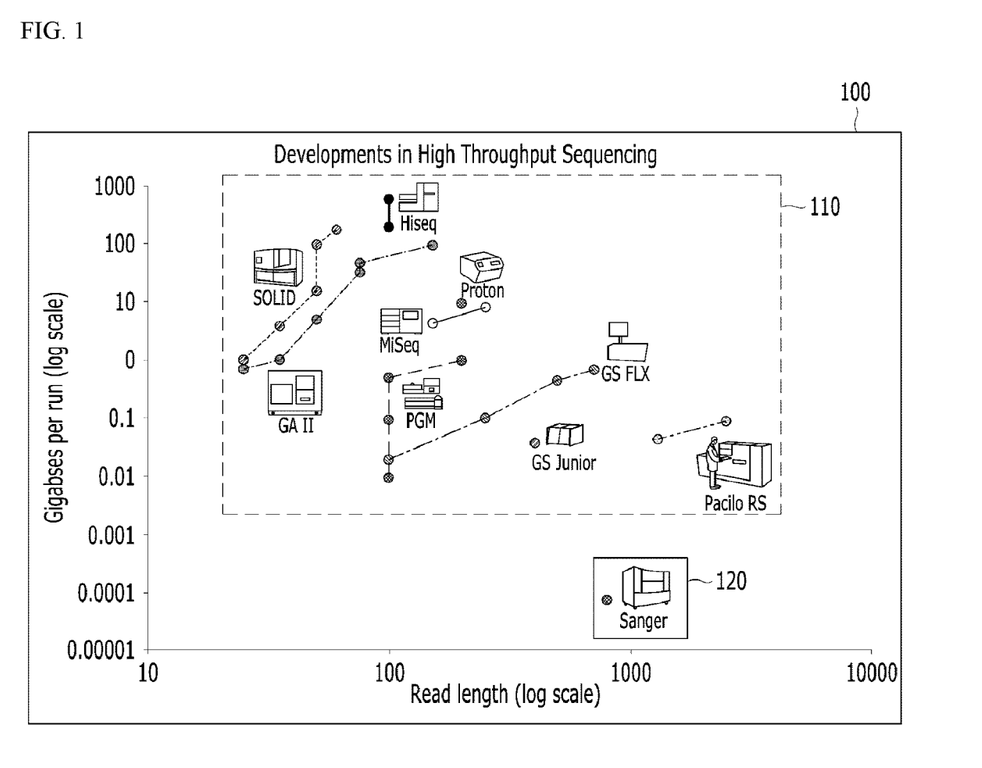
FIG. 1 is a diagram showing a graph for comparing a next-generation sequencing method and a conventional sequencing method.

Referring to FIG. 1, a graph 100 for comparing NGS 110 and Sanger sequencing 120 is shown. As shown in the graph 100, the NGS 110 may have higher performance than the Sanger sequencing 120. Meanwhile, as can be seen from the horizontal axis of the graph 100, the NGS 110 may have various read lengths.

The NGS may be used to sequence a cancer patient's DNA to detect mutations. Mutations may be detected in cancer tissue through various software applications that sequence DNA through the NGS.

When a mutation is detected by conventional software, and particularly, when DNA is sequenced with a specific sequencing platform such as short-read sequencing, there may occur a false positive in which, although there are no mutations, the mutation is falsely detected due to the nature of the sequencing platform. Such a sequencing platform-specific false positive may degrade the accuracy of mutation detection.

Therefore, in order to prevent the accuracy of mutation detection from being degraded by the sequencing platform-specific false positive, there may be a need to improve the mutation detection method.

DISCLOSURE

Technical Problem

A technical object to be achieved by the present disclosure is to improve mutation detection performance by solving a problem which is caused by conventional software and in which the accuracy of mutation detection is degraded due to a sequencing platform-specific false positive.

Technical Solution

According to an aspect of the present disclosure, there is provided a mutation detection apparatus including a memory configured to store software for implementing a neural network and a processor configured to detect a mutation by executing the software, wherein the processor is configured to generate first genome data extracted from a target tissue and second genome data extracted from a normal tissue, extract image data by preprocessing the first genome data and the second genome data, and detect a mutation of the target tissue on the basis of the image data through the neural network trained to correct a sequencing platform-specific false positive.

According to another aspect of the present disclosure, there is provided a method of detecting a mutation by executing software for implementing a neural network, the method including generating first genome data extracted from a target tissue and second genome data extracted from a normal tissue, extracting image data by preprocessing the first genome data and the second genome data; and detecting a mutation of the target tissue on the basis of the image data through the neural network trained to correct a sequencing platform-specific false positive.

Advantageous Effects

With the apparatus and method according to the present disclosure, the neural network may be used during a process of detecting mutations and may be trained in advance to correct a sequencing platform-specific false positive. Thus, it is possible to prevent the accuracy of mutation detection from being degraded due to the sequencing platform-specific false positive. In particular, unlike conventional statistical methods, a neural network may be used to detect mutations, and thus it is possible to detect mutations with high performance compared to the conventional methods.

MODE FOR CARRYING OUT THE INVENTION

Hereinafter, embodiments of the present disclosure will be described in detail with reference to the accompanying drawings. The following description is only for specifying the embodiments and is not intended to limit or restrict the scope of the present disclosure. What those skilled in the art can easily infer from the detailed description and embodiments of the present disclosure should be construed as falling within the scope of the present disclosure.

The terms used herein are described as general terms widely used in the technical field related to the present disclosure, but the meanings of the terms may be altered according to the intent of a technician in this field, the emergence of new technology, examination criteria, precedents, or the like. Some of the terms may be arbitrarily selected by the applicant, and in this case, the meanings of the arbitrarily selected terms will be described in detail. The terms used herein should not be interpreted as being limited to dictionary definitions, but should be interpreted as having meanings reflecting the overall context of the specification.

The term "comprising" or "including" used herein should be construed as not necessarily including all of the elements or operations disclosed herein and should be construed as including the exclusion or addition of some elements or operations.

Although terms including ordinal numbers such as "first" and "second" may be used herein to describe various elements or operations, these elements or operations should not be limited by these terms. Terms including ordinal numbers should be construed only for the purpose of distinguishing one element or operation from other elements or operations.

Hereinafter, embodiments of the present disclosure will be described in detail with reference to the accompanying drawings. Detailed descriptions of matters well known to those skilled in the art will be omitted.

Figure 2:
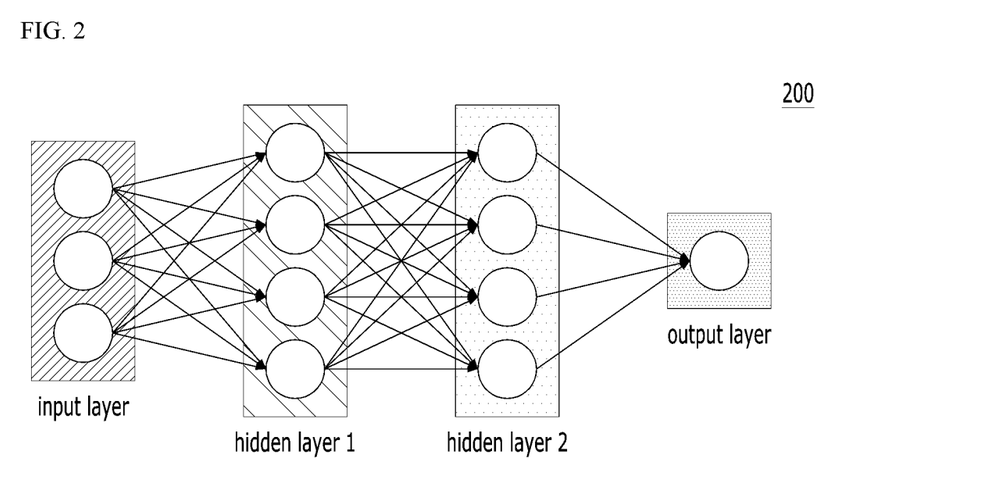
FIG. 2 is a diagram illustrating a neural network according to an embodiment.

FIG. 2 is a diagram illustrating a neural network according to an embodiment.

Referring to FIG. 2, elements constituting a neural network 200 are shown. The neural network 200 is an artificially implemented neural network and has a hidden layer in addition to an input layer and an output layer to efficiently perform various nonlinear functions. The neural network 200 may include a plurality of hidden layers and correspond to a deep neural network. In addition to the structure illustrated in FIG. 2, the neural network 200 may be implemented with various architectures such as a recurrent neural network (RNN) or a convolutional neural network (CNN).

The neural network 200 may be trained by adjusting values of various parameters constituting the neural network 200. When the neural network 200 is properly trained according to various machine learning and deep learning methods, the neural network 200 may perform a function corresponding to the training purpose with high performance. Accordingly, the neural network 200 may be widely used in various fields in addition to fields such as speech recognition, natural language processing, and image analysis. In particular, as in the present disclosure, the neural network 200 may be utilized to solve conventional problems, such as mutation detection, in the bio field.

Figure 3:
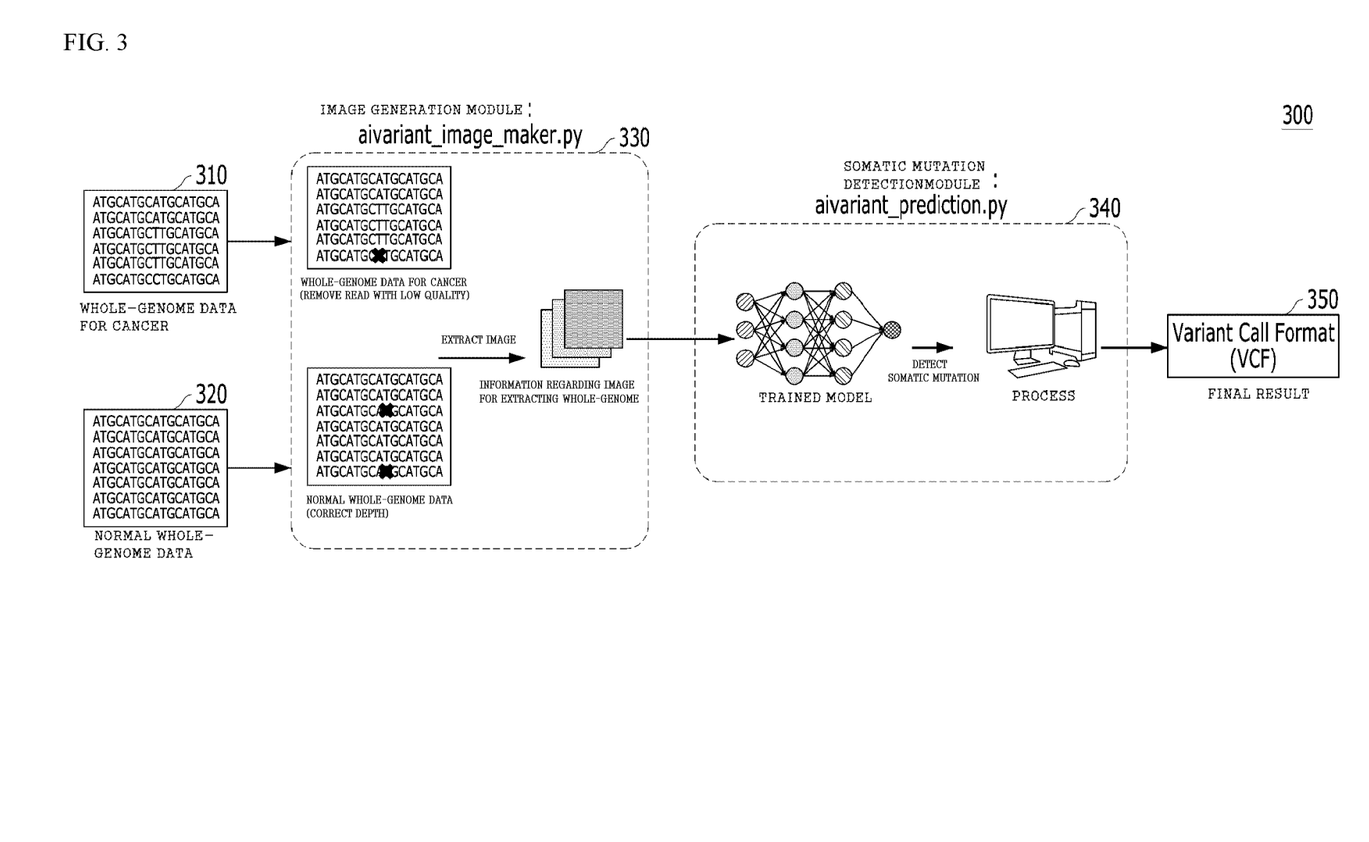
FIG. 3 is a diagram illustrating a process of detecting a mutation according to an embodiment.

FIG. 3 is a diagram illustrating a process of detecting a mutation according to an embodiment.

Referring to FIG. 3, a series of processing processes on first genome data 310 and second genome data 320 may be performed in a mutation detection apparatus 300 to generate a mutation detection result 350. As described below, the mutation detection apparatus 300 may be implemented as an apparatus 400 of FIG. 4.

The series of processing processes in the apparatus 300 may be implemented in the form of software or programs. Each operation of the series of processing processes in the apparatus 300 may be implemented with a module for performing a specific function, such as an image generation module 330 or a mutation detection module 340. For example, the software for implementing the series of processing processes may be implemented with a Python script and may be executed in an environment such as LINUX CentOS release 7.6.

The first genome data 310 may refer to genome data extracted from a target tissue. The target tissue is a tissue from which a mutation is to be detected and may refer to a cancer tissue. The second genome data 320 may refer to genome data extracted from a normal tissue.

In order to accurately determine a gene with a mutation from among genes of the target tissue, the second genome data 320 may be considered in addition to the first genome data 310. Meanwhile, although not shown in FIG. 3, a process of extracting the first genome data 310 from the target tissue and a process of extracting the second genome data 320 from the normal tissue may be implemented with a separate software module in the apparatus 300.

In the apparatus 300, a mutation is not detected in a statistical manner solely on the basis of genome data of a cancer patient. The first genome data 310 and the second genome data 320 may be extracted from a tissue where a cancer actually originates and a normal tissue which is subject to comparison, and a mutation may be detected. Thus, individual characteristics that may differ for each cancer patient and cancer tissue may be reflected in the mutation detection process. Therefore, it is possible to more accurately detect a gene with a mutation from among genes of a cancer tissue.

The image generation module 330 may extract image data from the first genome data 310 and the second genome data 320. The image data may refer to data obtained by visualizing the first genome data 310 and the second genome data 320 such that the image data can be provided to the neural network 200 trained to detect mutations.

The mutation detection module 340 may detect a mutation of a target tissue on the basis of the image data. To this end, the neural network 200 may be implemented in the mutation detection module 340, and the neural network 200 may be trained to detect a gene with a mutation among from genes of the target tissue. For example, as will be described below with reference to FIGS. 5 and 6, the neural network 200 may be implemented with a convolutional neural network (CNN) that is trained to extract a feature from an image and perform a specific function on the basis of the feature.

The mutation detection module 340 may perform additional processing on an output of the neural network 200 to generate the mutation detection result 350. The mutation detection result 350 may be generated in a standard format (e.g., the Variant Call Format (VCF)) that displays information of a gene determined as having a mutation through a comparison to a reference gene.

With the apparatus 300, the neural network 200 trained for a specific purpose may be utilized to detect mutations, and thus it is possible to improve the accuracy of mutation detection. As will be described below, the neural network 200 may be trained to correct a sequencing platform-specific false positive, and thus it is possible to prevent a decrease in accuracy due to a false positive which has been pointed out as a problem in conventional mutation detection software.

Meanwhile, the mutation detected from the target tissue by the apparatus 300 may be a somatic single nucleotide variant (sSNV). The sSNV is a somatic mutation and may mean that a mutation has occurred in only a single nucleotide among nucleotides constituting a nucleotide sequence. The sSNV may be suitable to be detected by the NGS and, in particular, may be suitable to be detected by the neural network 200 trained to correct a sequencing platform-specific false positive. However, the present disclosure is not limited thereto, and other types of mutations may be detected by the apparatus 300 in addition to the sSNV.

Figure 4:
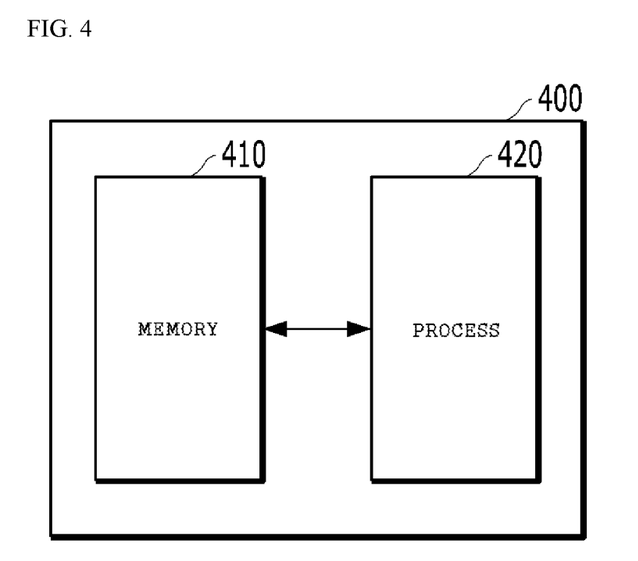
FIG. 4 is a block diagram showing elements constituting a mutation detection apparatus according to an embodiment.

FIG. 4 is a block diagram showing elements constituting a mutation detection apparatus according to an embodiment.

Referring to FIG. 4, a mutation detection apparatus 400 may include a memory 410 and a processor 420. However, the present disclosure is not limited thereto, and the apparatus 400 may further include other general-purpose elements in addition to the elements shown in FIG. 4. Meanwhile, the apparatus 400 of FIG. 4 may be an example of implementing the apparatus 300 of FIG. 3.

The apparatus 400 may correspond to various devices configured to detect mutations. For example, the apparatus 400 may be various kinds of computing devices such as personal computers (PCs), server devices, smartphones, tablet PCs, and other mobile devices.

The memory 410 may store software for implementing the neural network 200. For example, data on layers and nodes constituting the neural network 200, computations performed by the nodes, and parameters applied to computation processes may be stored in the memory 410 in at least one instruction, program, or software.

The memory 410 may be implemented with a non-volatile memory such as read only memory (ROM), programmable ROM (PROM), electrically programmable ROM (EPROM), electrically erasable and programmable ROM (EEPROM), flash memory, phase-change RAM (PRAM), magnetic RAM (MRAM), resistive RAM (RRAM), and ferroelectric RAM (FRAM) or may be implemented with a volatile memory such as dynamic RAM (DRAM), static RAM (SRAM), synchronous DRAM (SDRAM), phase-change RAM (PRAM), resistive RAM (RRAM), and ferroelectric RAM (FeRAM). Also, the memory 410 may be implemented with a hard disk drive (HDD), solid-state drive (SSD), secure digital (SD), or micro secure digital (Micro-SD).

The processor 420 may detect mutations by executing the software stored in the memory 410. The processor 420 may detect a mutation of a target tissue by performing a series of processing processes for mutation detection. The processor 420 may perform an overall function for controlling the apparatus 400 and may process various kinds of computations in the apparatus 400.

The processor 420 may be implemented with an array of multiple logic gates or a general-purpose microprocessor. The processor 420 may include a single processor or a plurality of processors. The processor 420 may be formed integrally with the memory 410 for storing software rather than separately from the memory 410. The processor 420 may be at least one of a central processing unit (CPU), a graphics processing unit (GPU), and an application processor (AP) included in the apparatus 400. However, this is only an example, and the processor 420 may be implemented in various other forms.

The processor 420 may generate first genome data extracted from a target tissue and generate second genome data extracted from a normal tissue. The processor 420 may embed a result dataset obtained by sequencing the target tissue into genome data to extract the first genome data and may embed a result dataset obtained by sequencing the normal tissue into genome data to extract the second genome data.

For example, the processor 420 may generate the first genome data and the second genome data through the HCC1143 cell line or the like. Meanwhile, the first genome data and the second genome data may be whole-genome data.

The processor 420 may extract image data by preprocessing the first genome data and the second genome data. The processor 420 may perform the preprocessing such that the first genome data and the second genome data have a form suitable to be processed by the neural network 200.

As an example, the first genome data and the second genome data may be converted into an image form such as image data. However, the conversion into the image form is only an example, and the first genome data and the second genome data may be converted into various forms other than an image depending on how the neural network 200 is implemented.

The processor 420 may perform the preprocessing by correcting the first genome data and the second genome data on the basis of mapping quality and depth. The processor 420 may remove reads with low quality with respect to the mapping quality and may adjust the depth of the first genome data and the second genome data. Through such a preprocessing process, the processor 420 may generate image data having a format suitable to be processed in the neural network 200.

The processor 420 may detect a mutation of the target tissue on the basis of the image data through the neural network 200 trained to correct a sequencing platform-specific false positive. By utilizing the trained neural network 200, the processor 420 may detect which gene of the target tissue has a mutation from the image data.

The sequencing platform may refer to a detailed method for sequencing the target tissue. The sequencing method may vary depending on what sequencing platform is applied. In the case of the NGS, the type of the sequencing platform may be determined according to the size of the DNA fragments, that is, according to the read length of the DNA fragments processed in parallel. For example, the sequencing platform may include long-read sequencing and short-read sequencing. However, the present disclosure is not limited to such classification based on the read length, and the sequencing platform may refer to various analysis methods for performing sequencing.

The neural network 200 may be trained in advance to receive image data and output a mutation of a target tissue. The trained neural network 200 may be stored in the memory 410 in the form of software, and the processor 420 may detect the mutation of the target tissue from the image data by executing the software for implementing the trained neural network 200.

The training of the neural network 200 may be performed by the apparatus 400. The apparatus 400 or the processor 420 may train the neural network 200 by repeatedly updating the values of the parameters constituting the neural network 200. Alternatively, the neural network 200 may be implemented with software after being trained outside the apparatus 400.

The neural network 200 may be trained to correct a sequencing platform-specific false positive. For example, the neural network 200 may be trained to a short-read sequencing-specific false positive, and the read length of the short-read sequencing may be 100 or less. However, the present disclosure is not limited to such a specific value, and the short-read sequencing may refer to a sequencing method having a read length shorter than that of the long-read sequencing.

The sequencing platform-specific false positive may refer to a case in which a mutation is detected in a specific gene according to a specific sequencing platform even though no mutation occurs in the gene. That is, the false positive may refer to a case in which a mutation is determined to have occurred according to a specific sequencing platform but the mutation is determined not to have occurred according to other sequencing platforms.

For example, a false positive specific to a specific sequencing platform may be a short-read sequencing-specific false positive. The short-read sequencing-specific false positive may refer to an error indicating that a mutation is detected according to the short-read sequencing but no mutation is detected according to the long-read sequencing.

When a short-read sequencing-specific false positive is present, it may be falsely determined that a mutation has occurred in a gene that actually has no mutations, and thus the accuracy of mutation detection may be degraded.

Since the neural network 200 may be trained to correct a sequencing platform-specific false positive, it is possible to improve the accuracy of mutation detection when a mutation of a target tissue is detected using the neural network 200. The details about the training of the neural network 200 will be described below with reference to FIGS. 5 and 6.

Figure 5:
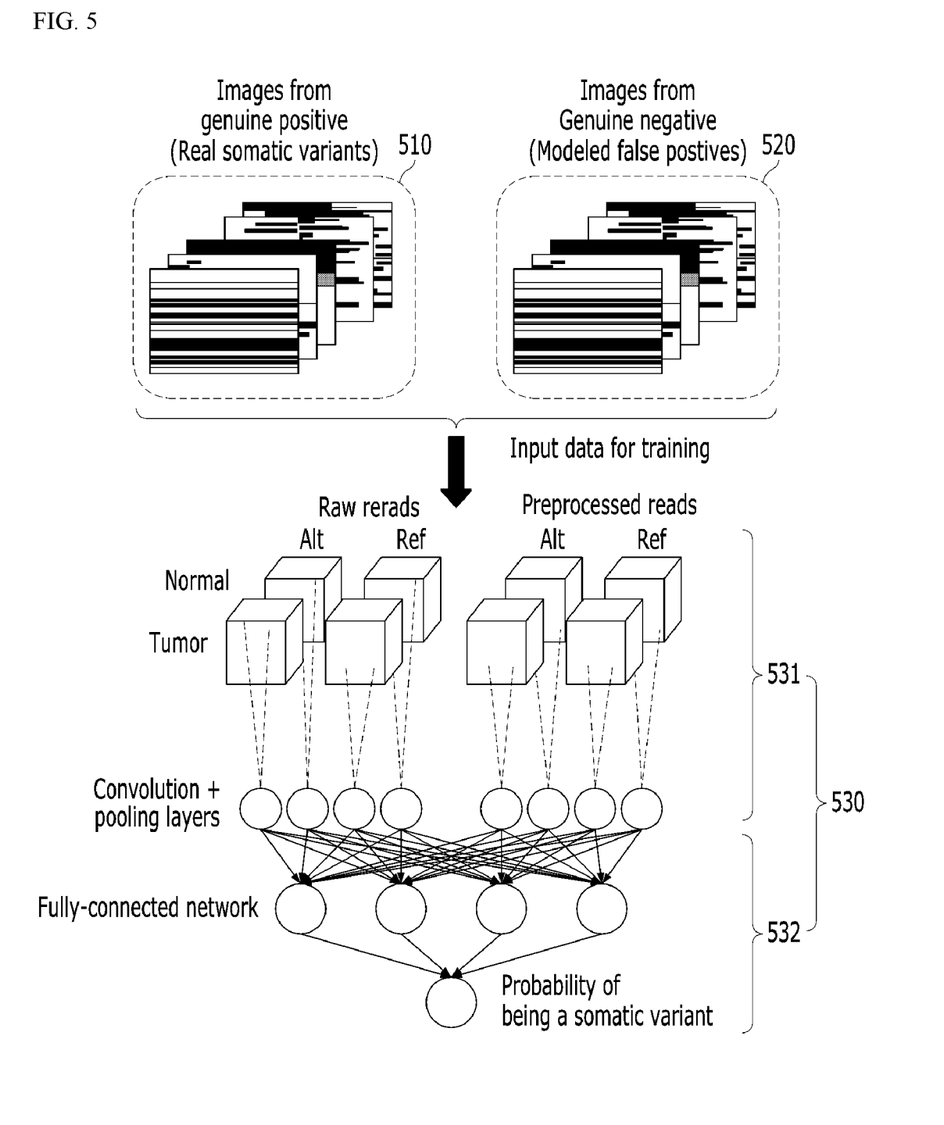
FIG. 5 is a diagram illustrating a structure of and a training method for a neural network according to an embodiment.

FIG. 5 is a diagram illustrating a structure of and a training method for a neural network according to an embodiment.

Referring to FIG. 5, the structure of a neural network 530 and a process of training the neural network 530 on the basis of first training image data 510 and second training image data 520 are illustrated. The neural network 530 of FIG. 5 may be an example in which the neural network 200 described with reference to FIGS. 2 to 4 is implemented.

As described above, the neural network 530 may be a convolutional neural network that extracts features from the image data and computes a probability that genes of the target tissue correspond to mutations on the basis of the features.

The neural network 530 may be implemented with a convolutional neural network (CNN) including a first network 531 and a second network 532. The first network 531 may include a convolutional layer and a pooling layer, and the second network 532 may include a fully connected network. When the training of the neural network 530 is completed, the first network 531 may extract a feature indicating the characteristic of input data from the input data, and the second network 532 may perform a function corresponding to the purpose of the neural network on the basis of the feature.

As described above, the training of the neural network 530 may be performed by the apparatus 400. Alternatively, after the training of the neural network 530 is completed outside the apparatus 400, only inference of the neural network 530 may be performed in the apparatus 400.

The neural network 530 may be trained using the first training image data 510 and the second training image data 520 as training data. Specifically, the neural network 530 may be trained to distinguish actual mutations from misdetected mutations on the basis of the first training image data 510 indicating training data on the actual mutations and the second training image data 520 indicating training data on the misdetected mutations due to a false positive.

The first training image data 510 may indicate training data on actual mutations. An actual mutation may refer to a case in which what is determined as a mutation according to one sequencing platform is also determined as a mutation according to other sequencing platforms. For example, an actual mutation may refer to a case in which what is determined as a mutation by the short-read sequencing is also determined as a mutation by the long-read sequencing.

The second training image data 520 may indicate training data on misdetected mutations due to a false positive. As described above, what is not actually a mutation may be falsely detected as a mutation according to a specific sequencing platform, and thus the neural network 530 may be trained to correct a false positive by using the misdetected mutations due to the false positive. For example, a misdetected mutation may refer to a case in which it is determined according to the long-read sequencing that there is no mutation but it is determined according to the short-read sequencing that there is a mutation.

In order to train the neural network 530, the first training image data 510 and the second training image data 520 may be used as train data, and thus as a result of the training, the neural network 530 may be configured to correct a sequencing platform-specific false positive. Since both of the first training image data 510 and the second training image data 520 are set as training data, it is possible to improve the accuracy of the neural network 530 in detecting mutations.

Figure 6:
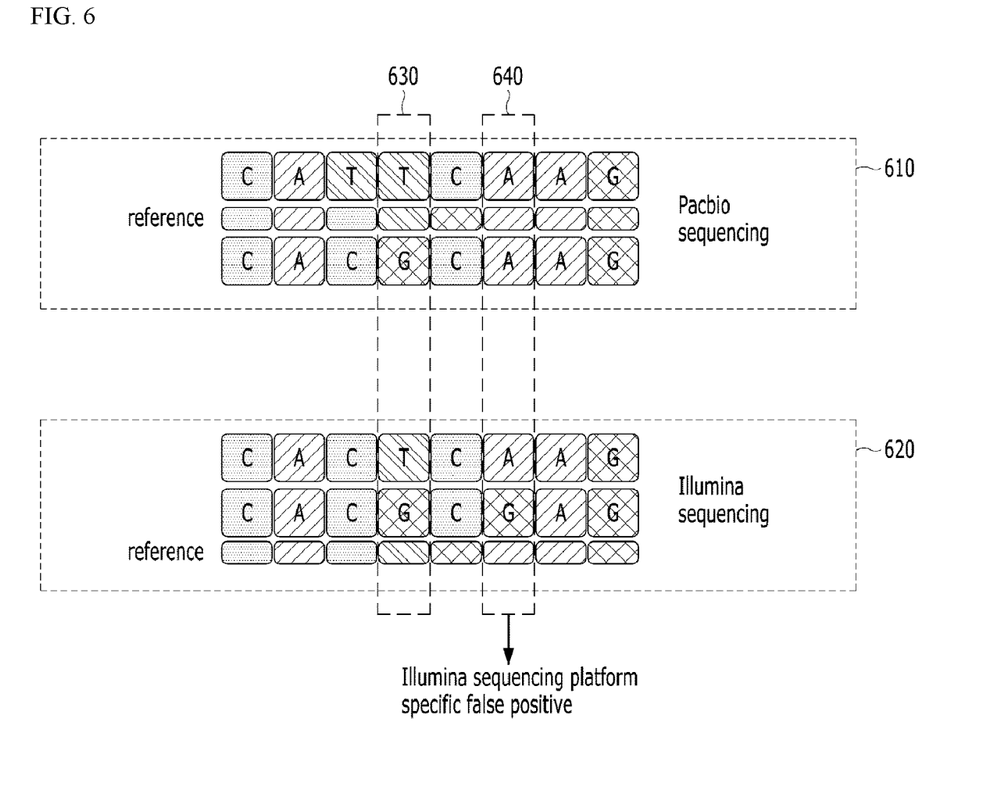
FIG. 6 is a diagram illustrating a process of generating data for training a neural network according to an embodiment.

FIG. 6 is a diagram illustrating a process of generating data for training a neural network according to an embodiment.

Referring to FIG. 6, long-read sequencing 610 and short-read sequencing 620 are illustrated as examples of different sequencing platforms for generating the first training image data 510 and the second training image data 520.

The first training image data 510 and the second training image data 520 may be generated based on results of performing the long-read sequencing 610 and the short-read sequencing 620 on the same training tissue. In order to secure training data for training the neural network 530, the long-read sequencing 610 and the short-read sequencing 620 may be performed on the same cancer tissue containing a gene with a mutation, and the results of the performance may be compared.

For example, PacBio sequencing may be performed as the long-read sequencing 610, and Illumina sequencing may be performed as the short-read sequencing 620. However, the present disclosure is not limited thereto, and other sequencing methods having appropriate lead lengths for short reads and long reads may be performed.

The results of performing the long-read sequencing 610 and the short-read sequencing 620 are illustrated in FIG. 6. For the same reference, there may be some differences between the mapping result by the long-read sequencing 610 and the mapping result by the short-read sequencing 620. For example, a comparison result 630 shows that both the long-read sequencing 610 and the short-read sequencing 620 determine that a mutation has occurred. In this case, a nucleotide corresponding to the comparison result 630 may be set as a mutation.

However, a comparison result 640 shows that the long-read sequencing 610 determines that no mutation occurs but the short-read sequencing 620 determines that a mutation has occurred. In this case, a nucleotide corresponding to the comparison result 640 may be set as a misdetected mutation due to a short-read sequencing-specific false positive.

Data on the actual mutation corresponding to the comparison result 630 may be labeled with the first training image data 510, and data on the misdetected mutation corresponding to the comparison result 640 may be labeled with the second training image data 520. The neural network 530 may be trained using the first training image data 510 and the second training image data 520 generated in the above-described way and thus may be trained to correct a false positive as in the comparison result 640.

Meanwhile, the data on the actual mutation corresponding to the comparison result 630 and the data on the misdetected mutation corresponding to the comparison result 640 may be implemented as virtual cancer tissue genome data through the HCC1143 cell line or the like. Through a process of obtaining information such as gene sequence, insertion/deletion (indel), and mapping quality from the virtual cancer tissue genome data, the first training image data 510 and second training image data 520 may be generated for the actual mutation and the misdetected mutation, respectively. That is, the first training image data 510 and the second training image data 520 may include at least one of the gene sequence, the indel, and the mapping quality.

Figure 7:
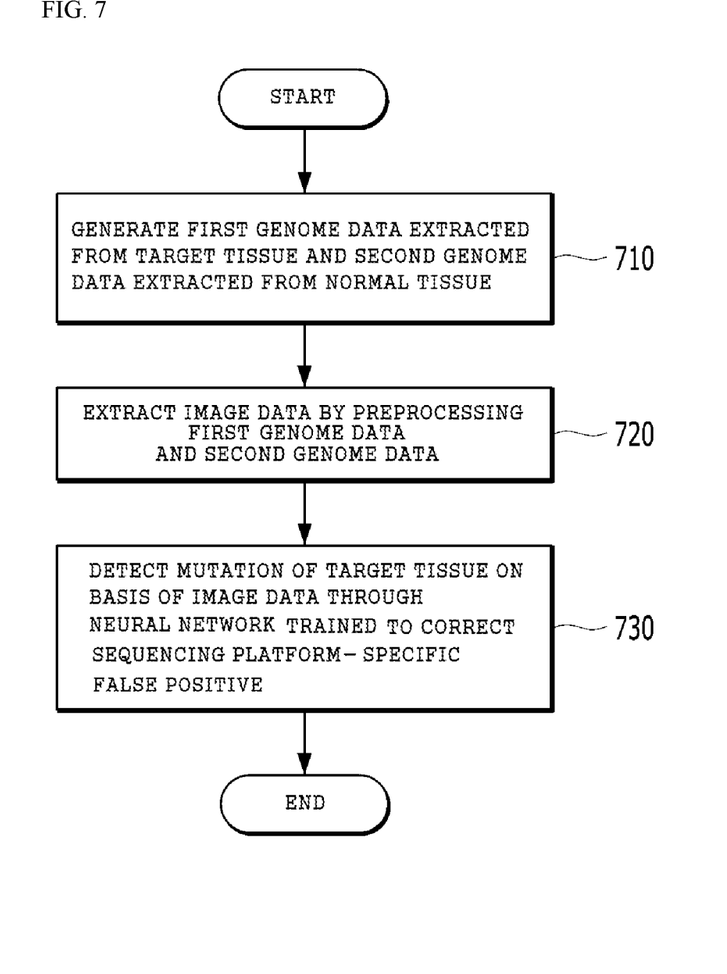
FIG. 7 is a flowchart illustrating operations constituting a mutation detection method according to an embodiment.

FIG. 7 is a flowchart illustrating operations constituting a method of generating a mutation according to an embodiment.

Referring to FIG. 7, the mutation detection method may include operations 710 to 730. However, the present disclosure is not limited thereto, and the mutation detection method may further include other general-purpose operations in addition to the operations shown in FIG. 7.

The mutation detection method of FIG. 7 may include operations performed in time series in the apparatus 300 or the apparatus 400 which has been described with reference to FIGS. 3 to 6. Therefore, the above description of the apparatus 300 or the apparatus 400 with reference to FIGS. 3 to 6 is equally applicable to the mutation detection method of FIG. 7 even when the description is omitted in the following description of the mutation detection method of FIG. 7.

In operation 710, the apparatus 400 may generate first genome data extracted from a target tissue and generate second genome data extracted from a normal tissue.

The apparatus 400 may perform the preprocessing by correcting the first genome data and the second genome data on the basis of mapping quality and depth.

In operation 720, the apparatus 400 may extract image data by preprocessing the first genome data and the second genome data.

In operation 730, the apparatus 400 may detect a mutation of the target tissue on the basis of the image data through a neural network trained to correct a sequencing platform-specific false positive.

The neural network may be trained to distinguish actual mutations from misdetected mutations on the basis of first training image data indicating training data on the actual mutations and second training image data indicating training data on the misdetected mutations due to a false positive.

The first training image data and the second training image data may be generated based on results of performing long-read sequencing and short-read sequencing on the same training tissue.

The first training image data and the second training image data may include at least one of gene sequence, indel, and mapping quality.

The neural network may be a convolutional neural network (CNN) that extracts features from the image data and computes a probability that genes of the target tissue correspond to mutations on the basis of the features.

The mutation detected from the target tissue may be a somatic single nucleotide variant (sSNV).

The mutation detection method of FIG. 7 may be recorded on a computer-readable recording medium on which at least one program or software including instruction for executing the method is recorded.

Examples of the computer-readable recording medium may include a magnetic medium, such as a hard disk, a floppy disk, and a magnetic tape, an optical medium, such as a compact disc read-only memory (CD-ROM), a digital versatile disc (DVD), etc., a magneto-optical medium such as a floptical disk, and a hardware device specially configured to store and perform program instructions, for example, a read-only memory (ROM), a random access memory (RAM), a flash memory, etc. Examples of the program instructions may include high-level language codes that can be executed by a computer using an interpreter as well as machine language codes such as those produced by a compiler.

Although the embodiments of the present disclosure have been described in detail, the scope of the present disclosure is not limited thereto, and several variations and modifications made by those skilled in the art using the basic concept of the present disclosure defined in the appended claims should be construed as falling within the scope of the present disclosure.

The invention claimed is:

1. A mutation detection apparatus comprising:
a memory configured to store software for implementing a neural network; and
a processor configured to detect a mutation by executing the software,
wherein the processor is configured to:
generate first genome data extracted from a target tissue and second genome data extracted from a normal tissue;
extract image data by preprocessing the first genome data and the second genome data; and
detect a mutation of the target tissue on the basis of the image data through the neural network trained to correct a sequencing platform-specific false positive.

2. The mutation detection apparatus of claim 1, wherein the neural network is trained to distinguish normal mutations from misdetected mutations on the basis of first training image data indicating training data on the normal mutations, which are normally detected, and second training image data indicating training data on the misdetected mutations, which are due to the false positive.

3. The mutation detection apparatus of claim 2, wherein the first training image data and the second training image data are generated based on results of performing long-read sequencing and short-read sequencing on the same training tissue.

4. The mutation detection apparatus of claim 2, wherein the first training image data and the second training image data include at least one of gene sequence, insertion and deletion (indel), and mapping quality.

5. The mutation detection apparatus of claim 1, wherein the neural network is a convolutional neural network (CNN) configured to extract features from the image data and compute a probability that genes of the target tissue correspond to mutations on the basis of the features.

6. The mutation detection apparatus of claim 1, wherein the processor performs preprocessing by correcting the first genome data and the second genome data on the basis of mapping quality and depth.

7. The mutation detection apparatus of claim 1, wherein the mutation detected from the target tissue is a somatic single nucleotide variant (sSNV).

8. A method of detecting a mutation by executing software for implementing a neural network, the method comprising:
generating first genome data extracted from a target tissue and second genome data extracted from a normal tissue;
extracting image data by preprocessing the first genome data and the second genome data; and
detecting a mutation of the target tissue on the basis of the image data through the neural network trained to correct a sequencing platform-specific false positive.

9. The method of claim 8, wherein the neural network is trained to distinguish normal mutations from misdetected mutations on the basis of first training image data indicating training data on the normal mutations, which are normally detected, and second training image data indicating training data on the misdetected mutations, which are due to the false positive.

10. The method of claim 9, wherein the first training image data and the second training image data are generated based on results of performing long-read sequencing and short-read sequencing on the same training tissue.

11. The method of claim 9, wherein the first training image data and the second training image data include at least one of gene sequence, insertion and deletion (indel), and mapping quality.

12. The method of claim 8, wherein the neural network is a convolutional neural network (CNN) configured to extract features from the image data and compute a probability that genes of the target tissue correspond to mutations on the basis of the features.

13. The method of claim 8, wherein the extracting of the image data comprises performing the preprocessing by correcting the first genome data and the second genome data on the basis of mapping quality and depth.

14. The method of claim 8, wherein the mutation detected from the target tissue is a somatic single nucleotide variant (sSNV).

* * * * *

UNITED STATES PATENT AND TRADEMARK OFFICE
CERTIFICATE OF CORRECTION

PATENT NO. : 11,640,662 B2  
APPLICATION NO. : 17/261164  
DATED : May 2, 2023  
INVENTOR(S) : Beak et al.

Page 1 of 1

It is certified that error appears in the above-identified patent and that said Letters Patent is hereby corrected as shown below:

On the Title Page

Item (12), should read BAEK et al.

Item (72) Inventors: "Dae Hyun BEAK, Seoul (KR); Jun Hak Ahn, Seoul (KR); Hyeon Seong Jeon, Seoul (KR); Do Yeon Kim, Seoul (KR)" should be changed to --Daehyun BAEK, Seoul (KR); Junhak AHN, Seoul (KR); Hyeonseong JEON, Seoul (KR); Doyeon KIM, Seoul (KR)--

Signed and Sealed this  
Eighth Day of October, 2024

Katherine Kelly Vidal  
*Director of the United States Patent and Trademark Office*